United States Patent
Lehr

(10) Patent No.: US 7,439,362 B2
(45) Date of Patent: Oct. 21, 2008

(54) PIPERAZINYL- OR PIPERIDINYLAMINE-SULFAMIC ACID AMIDES AS INHIBITORS OF STEROID SULFATASE

(75) Inventor: Philipp Lehr, Moedling (AT)

(73) Assignee: Novartis AG, Basel (CH)

( * ) Notice: Subject to any disclaimer, the term of this patent is extended or adjusted under 35 U.S.C. 154(b) by 445 days.

(21) Appl. No.: 10/509,259

(22) PCT Filed: Mar. 27, 2003

(86) PCT No.: PCT/EP03/03214

§ 371 (c)(1), (2), (4) Date: May 3, 2005

(87) PCT Pub. No.: WO03/082842

PCT Pub. Date: Oct. 9, 2003

(65) Prior Publication Data

US 2006/0052393 A1 Mar. 9, 2006

(30) Foreign Application Priority Data

Mar. 28, 2002 (GB) ................ 0207500.0
Nov. 4, 2002 (GB) ................ 0225679.0

(51) Int. Cl.
*C07D 241/04* (2006.01)
*C07D 295/00* (2006.01)

(52) U.S. Cl. .................... 544/383

(58) Field of Classification Search ........ None
See application file for complete search history.

(56) References Cited

U.S. PATENT DOCUMENTS

| | | | | |
|---|---|---|---|---|
| 4,244,950 A | 1/1981 | De Ridder et al. | ....... | 424/248.5 |
| 5,256,632 A | 10/1993 | Wolf et al. | ........... | 504/252 |
| 5,807,878 A | 9/1998 | Corbier et al. | ........... | 514/385 |
| 5,977,155 A | 11/1999 | Corbier et al. | ........... | 514/398 |
| 6,087,304 A | 7/2000 | Brendel et al. | ........... | 504/244 |
| 6,600,072 B2 | 7/2003 | Brendel et al. | ........... | 564/165 |
| 7,067,507 B2 * | 6/2006 | Pulley et al. | ........... | 514/183 |
| 2002/0091116 A1 | 7/2002 | Zhu et al. | ........... | 514/211.15 |

FOREIGN PATENT DOCUMENTS

| | | | |
|---|---|---|---|
| DE | 876846 | * | 5/1953 |
| EP | 0 089 089 | | 9/1983 |
| EP | 399556 | * | 11/1990 |
| EP | 0 478 328 | | 4/1992 |
| EP | 1 122 242 | | 8/2001 |
| GB | 2 103 610 | | 2/1983 |
| WO | 95/25443 | | 9/1995 |
| WO | 96/02530 | | 2/1996 |
| WO | 96/10559 | | 4/1996 |
| WO | 97/20820 | | 6/1997 |
| WO | 98/46626 | | 10/1998 |
| WO | 00/51547 | | 9/2000 |
| WO | 00/71516 | | 11/2000 |
| WO | 01/83459 | | 11/2001 |
| WO | 03/004487 | | 1/2003 |

OTHER PUBLICATIONS

"Cancer definition" http://www.medterms.com/script/main/art.asp?articlekey<2580, accessed Nov. 6, 2007.*
"Prophylaxis definition", http://www.medterms.com/script/main/art.asp?articlekey=12063, accessed Nov. 6, 2007.*
Effenberger et al., "Aminobenzenes. III. Reaction of Activated Aromatic Compounds and Isocyanates", Chemische Berichte, vol. 101, No. 2, pp. 502-511 (1968), Caplus Abstract No. 1968:68617.
Poirier et al., "Steroid Sulfatase Inhibitors", Expert Opinion on Therapeutic Patents, vol. 9, No. 8, pp. 1083-7099 (1999).
Purohit et al., "Recent Advances in the Development of Steroid Sulphatase Inhibitors", Journal of Steroid Biochemistry and Molecular Biology, vol. 69, No. 1/6, pp. 227-238 (1999).

* cited by examiner

*Primary Examiner*—James O. Wllson
*Assistant Examiner*—Noble Jarrell
(74) *Attorney, Agent, or Firm*—Novartis; John B. Alexander

(57) ABSTRACT

Piperazinyl- or piperidinylamine-sulfamic acid amides and their use for the manufacture of a medicament in diseases mediated by the action of steriod sulfatase.

8 Claims, No Drawings

PIPERAZINYL- OR PIPERIDINYLAMINE-SULFAMIC ACID AMIDES AS INHIBITORS OF STEROID SULFATASE

The present invention relates to sulfamic acid amides, e.g. useful in the treatment of disorders mediated by the action of steroid sulfatase.

In one aspect the present invention provides a compound of formula

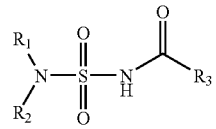

I wherein either
- $R_1$ and $R_2$ together with the nitrogen atom to which they are attached are piperazinyl, wherein the second nitrogen atom is substituted by $(C_{1-6})$alkoxycarbonyl or by $(C_{6-18})$aryl, which $(C_{6-18})$aryl is substituted by one or more halogen, $(C_{1-6})$haloalkyl, e.g. $CF_3$, aminocarbonyl;

or
- $R_1$ is hydrogen and $R_2$ is piperidinyl, attached via a carbon atom of the piperidinyl ring, wherein the nitrogen atom is substituted by $(C_{1-6})$alkoxycarbonyl or by $(C_{6-18})$aryl, and
- $R_3$ is $(C_{6-18})$aryl or $(C_{6-18})$aryl$(C_{1-4})$alkyl, which aryl is substituted by one or more halogen, aminocarbonyl, or $(C_{1-6})$haloalkyl.

If not otherwise defined herein $(C_{6-18})$aryl, e.g. phenyl, such as $(C_{6-18})$aryl substituted by one or more halogen, $(C_{1-6})$haloalkyl, e.g. $CF_3$, or aminocarbonyl. $(C_{1-6})$Alkoxycarbonyl includes unsubstituted or substituted $(C_{1-6})$alkoxycarbonyl, e.g. alkoxycarbonyl wherein the alkyl group is substituted by $(C_{6-18})$aryl, such as phenyl, e.g. benzyloxycarbonyl. Halogen includes fluoro, chloro, bromo, iodo, e.g. fluoro, chloro. $(C_{6-18})$Aryl$(C_{1-4})$alkyl is preferably phenyl $(C_{1-4})$alkyl, e.g. phenylethyl, wherein phenyl is substituted as described for substituted $(C_{6-18})$aryl.

Preferably in a compound of formula I either
- $R_1$ and $R_2$ together with the nitrogen atom are piperazinyl, wherein the second nitrogen atom is substituted by
  - $(C_{1-6})$alkoxycarbonyl, e.g. tert.butoxycarbonyl, benzyloxycarbonyl,
  - phenyl substituted by aminocarbonyl, $(C_{1-6})$haloalkyl, or
- $R_1$ is hydrogen and $R_2$ is piperidinyl, attached via a carbon atom of the piperidinyl ring, wherein the nitrogen atom is substituted by
  - $(C_{1-6})$alkoxycarbonyl, e.g. tert.butoxycarbonyl, benzyloxycarbonyl,
  - phenyl substituted by aminocarbonyl, $(C_{1-6})$haloalkyl, and
- $R_3$ is phenyl substituted by one or more
  - halogen,
  - $(C_{1-6})$haloalkyl, e.g. $CF_3$,
  - aminocarbonyl,
  or
  - $(C_{1-4})$alkyl, substituted by phenyl, which phenyl is substituted by one or more
    - halogen,
    - $(C_{1-6})$haloalkyl, e.g. $CF_3$,
    - aminocarbonyl.

In another aspect the present invention provides a compound of formula I, which is selected from the group consisting of the compounds of formula

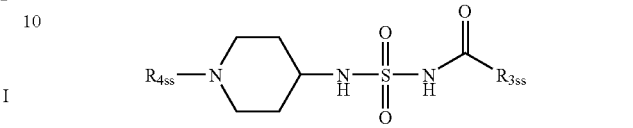

$I_{ss}$ wherein
a. $R_{3ss}$ is 3,5-bis(trifluoromethyl)phenyl and $R_{4ss}$ is 2-aminocarbonyl-5-trifluoromethylphenyl,
b. $R_{3ss}$ is 2,3-dichlorophenyl, $R_{4ss}$ is 2-aminocarbonyl-5-trifluoromethylphenyl,
c. $R_{3ss}$ is 3,5-dichlorophenyl $R_{4ss}$ is 2-aminocarbonyl-5-trifluoromethylphenyl, and
d. $R_{3ss}$ is 3,5-bis(trifluoromethyl)phenyl and $R_{4ss}$ is tert.butoxycarbonyl;

preferably $R_{3ss}$ is 3,5-bis(trifluoromethyl)phenyl.

In another aspect the present invention provides a compound of formula I, which is selected from the group consisting of compounds of formula

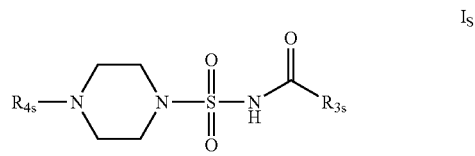

$I_s$ wherein
a. $R_{3s}$ is 3,5-bis(trifluoromethyl)phenyl and $R_{4s}$ is tert.butoxycarbonyl,
b. $R_{3s}$ is 2,3-dichlorophenyl and $R_{4s}$ is tert.butoxycarbonyl,
c. $R_{3s}$ is 3,5-dichlorophenyl and $R_{4s}$ is tert.butoxycarbonyl,
d. $R_{3s}$ is 3,5-bis(trifluoromethyl)phenyl and $R_{4s}$ is benzyloxycarbonyl,
e. $R_{3s}$ is 2,3-dichlorophenyl and $R_{4s}$ is benzyloxycarbonyl,
f. $R_{3s}$ is 3,5-dichlorophenyl and $R_{4s}$ is benzyloxycarbonyl,
g. $R_{3s}$ is 3,5-dichlorophenyl and $R_{4s}$ is benzyloxycarbonyl,
h. $R_{3s}$ is 3,5-bis(trifluoromethyl)phenyl and $R_{4s}$ is 2-aminocarbonyl-5-trifluoromethylphenyl,
i. $R_{3s}$ is 3,5-dichlorophenyl and $R_{4s}$ is is 2-aminocarbonyl-5-trifluoromethylphenyl,
j. $R_{3s}$ is 2,3-dichlorophenyl and $R_{4s}$ is is 2-aminocarbonyl-5-trifluoromethylphenyl, and
k. $R_{3s}$ is 2-(3,5-bis(trifluoromethyl)phenyl)ethyl and $R_{4s}$ is tert.butoxycarbonyl.

Compounds provided by the present invention are hereinafter designated as "compound(s) of (according to) the present invention". A compound of formula I includes a compound of formula $I_s$ and a compound of formula $I_{ss}$. Each single substituent defined above in a compound of the present invention may be per se a preferred substituent, independently of the other substituents defined. A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

A salt of a compound of the present invention includes a metal salt, an acid addition salt or an amine salt. Metal salts include for example alkali or earth alkali salts; acid addition salts include salts of a compound of the present invention with an acid, e.g. HCl; amine salts include salts of a compound of the present invention with an amine. A compound of the present invention in the form of a salt is preferably a metal salt.

A compound of the present invention in free form may be converted into a corresponding compound in the form of a salt; and vice versa. A compound of the present invention in free form or in the form of a salt and in the form of a solvate may be converted into a corresponding compound in free form or in the form of a salt in non-solvated form; and vice versa.

A compound of the present invention may exist in the form of isomers and mixtures thereof; e.g. optical isomers, diastereoisomers, cis/trans conformers. A compound of the present invention may e.g. contain asymmetric carbon atoms and may thus exist in the form of enatiomers or diastereoisomers and mixtures thereof, e.g. racemates. Any asymmetric carbon atom may be present in the (R)—, (S)— or (R,S)-configuration, preferably in the (R)— or (S)-configuration.

Isomeric mixtures may be separated as appropriate, e.g. according, e.g. analogously, to a method as conventional, to obtain pure isomers. The present invention includes a compound of the present invention in any isomeric form and in any isomeric mixture.

The present invention also includes tautomers of a compound of formula I, where tautomers can exist.

Any compound described herein, e.g. a compound of the present invention, may be prepared as appropriate, e.g. according, e.g. analogously, to a method as conventional, e.g. or as specified herein.

In another aspect the present invention provides a process for the production of a compound of the present invention comprising the steps of either A. reacting a compound of formula

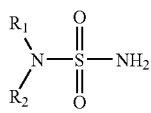

II wherein $R_1$ and $R_2$ are as defined above,
with a compound of formula

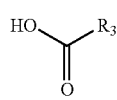

III wherein $R_3$ is as defined above, e.g. in an activated form, such as In the form of an carboxylic acid chloride, e.g. or reacting in the presence of a coupling agent;

or

B1. reacting a compound of formula II wherein $R_1$ and $R_2$ together with the nitrogen atom to which they are attached are unsubstituted piperazinyl with a compound of formula III, wherein $R_3$ is as defined above, e.g. in an activated form, such as in the form of an carboxylic acid chloride, e.g. or reacting in the presence of a coupling agent, to obtain a compound of formula

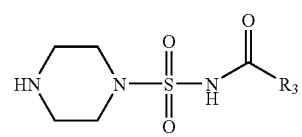

IV wherein $R_3$ is as defined above; and

B2. reacting a compound of formula IV with an optionally substituted $(C_{6-18})$fluoroaryl, e.g. a fluorophenyl, wherein optional aryl-substitutents are as defined in a compound of formula I, in the presence of a base, e.g. $K_2CO_3$, to obtain a compound of formula I, wherein $R_1$ and $R_2$ together with the nitrogen atom to which they are attached are piperazinyl which is substituted at the second nitrogen atom by optionally substituted $(C_{6-18})$aryl; or C1. reacting a compound of formula

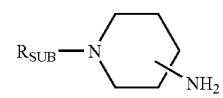

V wherein $R_{SUB}$ is $(C_{1-6})$alkoxycarbonyl, with benzaldehyde in the presence of $NaBH_4$, to obtain a compound of formula

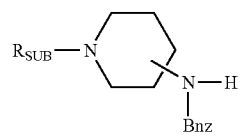

VI wherein $R_{SUB}$ is as defined above and Bnz is benzyl,

C2. reacting a compound of formula VI with $H_2N$—$SO_2$—$NH_2$ to obtain a compound of formula

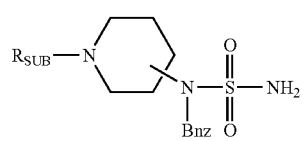

VII wherein $R_{SUB}$ and Bnz are as defined above,

C3. reacting a compound of formula VII with $R_3$—COOH, wherein $R_3$ is as defined above, e.g.

wherein the carboxyl group is in an activated form, to obtain a compound of formula

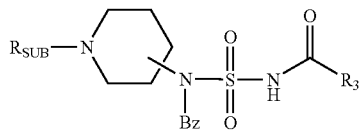

VIII wherein $R_{SUB}$, Bnz and $R_3$ are as defined above,

C4. reacting a compound of formula VIII with etheric HCl to obtain a compound of formula

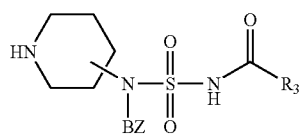

IX wherein Bnz and $R_3$ are as defined above,

C5. reacting a compound of formula IX with an optionally substituted $(C_{6-18})$fluoroaryl, e.g. a fluorophenyl, wherein optional aryl-substitutents are as defined in a compound of formula I, in the presence of a base, e.g. $K_2CO_3$, to obtain a compound of formula X, which is a compound of formula IX, wherein Bnz and $R_3$ are as defined above and the nitrogen of the piperidinyl is substituted by optionally substituted $(C_{6-18})$aryl, C6. hydrogenating a compound obtained in step C5, in the presence of a palladium catalyst, to obtain a compound of formula I, wherein $R_1$ is H, $R_2$ is piperidine substituted by optionally substituted $(C_{6-18})$aryl, and $R_3$ is as defined above, and isolating a compound of formula I obtained in reaction A, reaction step B2, or reaction step C6 from the reaction mixture.

Compounds of formula II, III, IV, V, VI, VII, VIII, IX and X are intermediates (starting materials) in the production of a compound of formula I. In such intermediates (starting materials) functional groups, if present, optionally may be in protected form or in the form of a salt, if a salt-forming group is present. Protecting groups, optionally present, may be removed at an appropriate stage, e.g. according, e.g. analogously, to a method as conventional. A compound of formula I thus obtained may be converted into another compound of formula I, e.g. or a compound of formula I obtained in free form may be converted into a salt of a compound of formula I and vice versa.

The above reactions may be carried out as appropriate, e.g. in appropriate solvent and at appropriate temperatures, e.g. according, e.g. analogously, to a method as conventional or according to a method as described herein. Intermediates (starting materials) are known or may be obtained appropriately, e.g. according to a method as conventional, e.g. or as described above. Any compound described herein, e.g. a compound of the present invention, may be prepared as appropriate, e.g. according, e.g. analogously, to a method as conventional, e.g. or as described herein.

Steroidal hormones in particular tissues are associated with several diseases, such as tumors of breast, endometrium and prostate and disorders of the pilosebaceous unit, e.g. acne, androgenetic alopecia, and hirsutism. Important precursors for the local production of these steroid hormones are steroid 3-O-sulfates which are desulfated by the enzyme steroid sulfatase in the target tissues. Inhibition of this enzyme results in reduced local levels of the corresponding active steroidal hormones, which is expected to be of therapeutic relevance. Furthermore, steroid sulfatase inhibitors may be useful as immunosuppressive agents, and have been shown to enhance memory when delivered to the brain.

Acne is a polyetiological disease caused by the interplay of numerous factors, such as inheritance, sebum, hormones, and bacteria. The most important causative factor in acne is sebum production; in almost all acne patients sebaceous glands are larger and more sebum is produced than in persons with healthy skin. The development of the sebaceous gland and the extent of sebum production is controlled hormonally by androgens; therefore, androgens play a crucial role in the pathogenesis of acne. In man, there are two major sources supplying androgens to target tissues: (i) the gonades which secrete testosterone, (ii) the adrenals producing dehydroepiandrosterone (DHEA) which is secreted as the sulfate conjugate (DHEAS). Testosterone and DHEAS are both converted to the most active androgen, dihydrotestosterone (DHT), in the target tissue, e.g. in the skin. There is evidence that these pathways of local synthesis of DHT in the skin are more important than direct supply with active androgens from the circulation. Therefore, reduction of endogeneous levels of androgens in the target tissue by specific inhibitors should be of therapeutic benefit in acne and seborrhoea. Furthermore, it opens the perspective to treat these disorders through modulation of local androgen levels by topical treatment, rather than influencing circulating hormone levels by systemic therapies.

Androgenetic male alopecia is very common in the white races, accounting for about 95% of all types of alopecia. Male-pattern baldness is caused by an increased number of hair follicles in the scalp entering the telogen phase and by the telogen phase lasting longer. It is a genetically determined hair loss effected through androgens. Elevated serum DHEA but normal testosterone levels have been reported in balding men compared with non-balding controls, implying that target tissue androgen production is important in androgenetic alopecia.

Hirsutism is the pathological thickening and strengthening of the hair which is characterized by a masculine pattern of hair growth in children and women. Hirsutism is androgen induced, either by increased formation of androgens or by increased sensitivity of the hair follicle to androgens. Therefore, a therapy resulting in reduction of endogeneous levels of androgens and/or estrogens in the target tissue (skin) should be effective in acne, androgenetic alopecia and hirsutism.

As described above, DHT, the most active androgen, is synthesized in the skin from the abundant systemic precursor DHEAS and the first step in the metabolic pathway from DHEAS to DHT is desulfatation of DHEAS by the enzyme steroid sulfatase to produce DHEA. The presence of the enzyme in keratinocytes and in skin-derived fibroblasts has been described. The potential use of steroid sulfatase inhibitors for the reduction of endogenous levels of steroid hormones in the skin was confirmed using known steroid sulfatase inhibitors, such as estrone 3-O-sulfamate and 4-methylumbelliferyl-7-O-sulfamate. We have found that inhibitors of placental steroid sulfatase also inhibit steroid sulfatase prepared from either a human keratinocyte (HaCaT) or a human skin-derived fibroblast cell line (1BR3GN). Such inhibitors were also shown to block steroid sulfatase in intact monolayers of the HaCaT keratinocytes.

Therefore, inhibitors of steroid sulfatase may be used to reduce androgen and estrogen levels in the skin. They can be used as inhibitors of the enzyme steroid sulfatase for the local treatment of androgen-dependent disorders of the pilosebaceous unit (such as acne, seborrhoea, androgenetic alopecia, hirsutism) and for the local treatment of squamous cell carcinoma.

Furthermore non-steroidal steroid sulfatase inhibitors are expected to be useful for the treatment of disorders mediated by the action of steroid hormones in which the steroidal products of the sulfatase cleavage play a role. Indications for these new kind of inhibitors include androgen-dependent disorders of the pilosebaceous unit (such as acne, seborrhea, androgenetic alopecia, hirsutism); estrogen- or androgen-dependent tumors, such as squamous cell carcinoma and neoplasms, e.g. of the breast, endometrium, and prostate; inflammatory and autoimmune diseases, such as rheumatoid arthritis, type I and II diabetes, systemic lupus erythematosus, multiple sclerosis, myastenia gravis, thyroiditis, vasculitis, ulcerative colitis, and Crohn's disease, psoriasis, contact dermatitis, graft versus host disease, eczema, asthma and organ rejection following transplantation. Steroid sulfatase inhibitors are also useful for the treatment of cancer, especially for the treatment of estrogen- and androgen-dependent cancers, such as cancer of the breast and endometrium and squamous cell carcinoma, and cancer of the prostata. Steroid sulfatase inhibitors are also useful for the enhancement of cognitive function, especially in the treatment of senile dementia, including Alzheimer's disease, by increasing the DHEAS levels in the central nervous system.

Activities of compounds in inhibiting the activity of steroid sulfatase may be shown in the following test systems:

Purification of Human Steroid Sulfatase

Human placenta is obtained freshly after delivery and stripped of membranes and connective tissues. For storage, the material is frozen at −70° C. After thawing, all further steps are carried out at 4° C., while pH values are adjusted at 20° C. 400 g of the tissue is homogenized in 1.2 l of buffer A (50 mM Tris-HCl, pH 7.4, 0.25 M sucrose). The homogenate obtained is centrifuged at 10,000×g for 45 minutes. The supernatant is set aside and the pellet obtained is re-homogenized in 500 ml of buffer A. After centrifugation, the two supernatants obtained are combined and subjected to ultracentrifugation (100,000×g, 1 hour). The pellet obtained is resuspended in buffer A and centrifugation is repeated. The pellet obtained is suspended in 50 ml of 50 mM Tris-HCl, pH 7.4 and stored at −20° C. until further work-up.

After thawing, microsomes are collected by ultracentrifugation (as described above) and are suspended in 50 ml of buffer B (10 mM Tris-HCl, pH 7.0, 1 mM EDTA, 2 mM 2-mercaptoethanol, 1% Triton X-100, 0.1% aprotinin). After 1 hour on ice with gentle agitation, the suspension is centrifuged (100,000×g, 1 hour). The supernatant containing the enzyme activity is collected and the pH is adjusted to 8.0 with 1 M Tris. The solution obtained is applied to a hydroxy apatite column (2.6×20 cm) and equilibrated with buffer B, pH 8.0. The column is washed with buffer B at a flow rate of 2 ml/min. The activity is recovered in the flow-through. The pool is adjusted to pH 7.4 and subjected to chromatography on a concanavalin A sepharose column (1.6×10 cm) equilibrated in buffer C (20 mM Tris-HCl, pH 7:4, 0.1% Triton X-100, 0.5 M NaCl). The column is washed with buffer C, and the bound protein is eluted with 10% methyl mannoside in buffer C. Active fractions are pooled and dialysed against buffer D (20 mM Tris-HCl, pH 8.0, 1 mM EDTA, 0.1% Triton X-100, 10% glycerol (v/v)).

The retentate obtained is applied to a blue sepharose column (0.8×10 cm) equilibrated with buffer D; which column is washed and elution is carried out with a linear gradient of buffer D to 2 M NaCl in buffer D. Active fractions are pooled, concentrated as required (Centricon 10), dialysed against buffer D and stored in aliquots at −20° C.

Assay of Human Steroid Sulfatase

It is known that purified human steroid sulfatase not only is capable to cleave steroid sulfates, but also readily cleaves aryl sulfates such as 4-methylumbelliferyl sulfate which is used in the present test system as an activity indicator. Assay mixtures are prepared by consecutively dispensing the following solutions into the wells of white microtiter plates:
1) 50 µl substrate solution (1.5 mM 4-methylumbelliferyl sulfate in 0.1 M Tris-HCl, pH 7.5)
2) 50 µl test compound dilution in 0.1 M Tris-HCl, pH 7.5, 0.1% Triton X-100 (stock solutions of the test compounds are prepared in DMSO; final concentrations of the solvent in the assay mixture not exceeding 1%)
3) 50 µl enzyme dilution (approximately 12 enzyme units/ml)

We define one enzyme unit as the amount of steroid sulfatase that hydrolyses 1 nmol of 4-methylumbelliferyl sulfate per hour at an initial substrate concentration of 500 µM in 0.1 M Tris-HCl, pH 7.5, 0.1% Triton X-100, at 37° C.

Plates are incubated at 37° C. for 1 hour. Then the reaction Is stopped by addition of 100 µl 0.2 M NaOH. Fluorescence intensity is determined in a Titertek Fluoroskan. II instrument with $\lambda_{ex}$=355 nm and $\lambda_{em}$=460 nm.

Calculation of Relative $IC_{50}$ Values

From the fluorescence intensity data (I) obtained at different concentrations (c) of the test compound in the human steroid sulfatase assay as described above, the concentration inhibiting the enzymatic activity by 50% ($IC_{50}$) is calculated using the equation:

$$I = \frac{I_{100}}{1 + (c/IC_{50})^s}$$

wherein $I_{100}$ is the intensity observed in the absence of inhibitor and s is a slope factor. Estrone sulfamate is used as a reference compound and its $IC_{50}$ value is determined in parallel to all other test compounds. Relative $IC_{50}$ values are defined as follows:

$$rel\ IC_{50} = \frac{IC_{50}\ of\ test\ compound}{IC_{50}\ of\ estrone\ sulfamate}$$

According to our testing and calculation estrone sulfamate shows an $IC_{50}$ value of approximately 60 nM.

The compounds of the present invention show activity in that described assay (rel $IC_{50}$ in the range of 0.0046 to 350).

CHO/STS Assay

CHO cells stably transfected with human steroid sulfatase (CHO/STS) are seeded into microtiter plates. After reaching approximately 90% confluency, they are incubated overnight with graded concentrations of test substances (e.g. compounds of the present invention). They are then fixed with 4% paraformaldehyde for 10 minutes at room temperature and washed 4 times with PBS, before incubation with 100 µl/well 0.5 mM 4-methylumbelliferyl sulfate (MUS), dissolved in 0.1 M Tris-HCl, pH 7.5. The enzyme reaction is carried out at 37° C. for 30 minutes. Then 50 µl/well stop solution (1 M Tris-HCl, pH 10.4) are added. The enzyme reaction solutions are transferred to white plates (Microfluor, Dynex, Chantilly, Va.) and read in a Fluoroskan II fluorescence microtiter plate reader. Reagent blanks are subtracted from all values. For drug testing, the fluorescence units (FU) are divided by the optical density readings after staining cellular protein with sulforhodamine B ($OD_{550}$), in order to correct for variations in cell number. $IC_{50}$ values are determined by linear interpolation between two bracketing points. In each assay with inhibitors, estrone 3-O-sulfamate is run as a reference compound, and the $IC_{50}$ values are normalized to estrone 3-O-sulfamate (relative $IC_{50}=IC_{50}$ compound/$IC_{50}$ estrone 3-O-sulfamate).

The compounds of the present invention show activity in that described assay (rel $IC_{50}$ in the range of 0.05 to 226).

Assay Using Human Skin Homogenate

Frozen specimens of human cadaver skin (about 100 mg per sample) are minced Into small pieces (about 1×1 mm) using sharp scissors. The pieces obtained are suspended in ten volumes (w/w) of buffer (20 mM Tris-HCl, pH 7.5), containing 0.1% Triton X-100. Test compounds (e.g. compounds of the present invention) are added at graded concentrations from stock solutions In ethanol or DMSO. Second, DHEAS as the substrate is added (1 μC/ml [$^3$H]DHEAS, specific activity: about 60 Ci/mmol, and 20 μM unlabeled DHEAS).

Samples are incubated for 18 hrs at 37° C. At the end of the Incubation period, 50 μl of 1 M Tris, pH 10.4 and 3 ml of toluene are added. A 1-ml aliquot of the organic phase is removed and subjected to liquid scintillation counting. The determined dpm-values in the aliquots are converted to nmol of DHEA cleaved per g of skin per hour.

The compounds of the present invention show activity in that described assay ($IC_{50}$ in the range of 0.03 to 10 μM).

A preferred compound of the present invention includes a compound of Example 1. That compound show in the Human Steroid Sulfatase Assay a rel $IC_{50}$ in the range of 0.0046 to 0.071, in the CHO/STS Assay a rel $IC_{50}$ in the range of 0.02 to 0.39, and in the Assay Using Human Skin Homogenate of an $IC_{50}$ in the range of 0.03 to 0.27 μM and is thus a highly active steroide sulfatase inhibitor.

The compounds of the present invention show activity in test systems as defined above. A compound of the present invention in salt and/or solvate form exhibits the same order of activity as a compound of the present invention in free and/or non-solvated form.

The compounds of the present invention are therefore indicated for use as steroid sulfatase inhibitors in the treatment of disorders mediated by the action of steroid sulfatase, e.g. including androgen-dependent disorders of the pilosebaceous unit, such as acne,
seborrhea,
androgenetic alopecia,
hirsutism;
cancers, such as estrogen and androgen-dependent cancers;
cognitive dysfunctions, such as senile dementia including Alzheimer's disease.

The compounds of the present invention are preferably used in the treatment of acne, seborrhea, androgenetic alopecia, hirsutism; estrogen, e.g. and androgen-dependent cancers, more preferably in the treatment of acne. Treatment includes therapeutical treatment and prophylaxis.

In another aspect the present invention provides the use of a compound of the present invention for the manufacture of a medicament, e.g. a pharmaceutical composition, for the treatment of disorders mediated by the action of steroid sulfatase, e.g. a disorder responsive to the inhibition of the action of steroid sulfatase, most preferably acne.

For such use a compound of the present invention includes one or more compounds of the present invention, e.g. a combination of two or more compounds of the present invention, preferably one.

In another aspect the present invention provides a compound of the present invention for use as a pharmaceutical.

In another aspect the present invention provides a method of treatment of disorders mediated by the action of steroid sulfatase, such as acne, seborrhea, androgenetic alopecia, hirsutism; cancers, such as estrogen and androgen-dependent cancers; cognitive dysfunctions, such as senile dementia including Alzheimer's disease, preferably acne, which treatment comprises administering to a subject in need of such treatment an effective amount of a compound of the present invention; e.g. in the form of a pharmaceutical composition.

Treatment includes treatment and prophylaxis.

For such treatment, the appropriate dosage will, of course, vary depending upon, for example, the chemical nature and the pharmakokinetic data of a compound of the present invention employed, the individual host, the mode of administration and the nature and severity of the conditions being treated. However, in general, satisfactory results may be obtained if the compounds are administered at a daily dose of from about 0.1 mg/kg to about 100 mg/kg animal body weight, e.g. conveniently administered In divided doses two to four times daily. For most mammals the total daily dosage is from about 5 mg to about 5000 mg, conveniently administered, for example, in divided doses up to four times a day or in retarded form. Unit dosage forms comprise, e.g. from about 1.25 mg to about 2000 mg of a compound of a present invention in admixture with at least one pharmaceutically acceptable excipient, e.g. carrier, diluent.

A compound of the present invention may be administered by any conventional route, for example enterally, e.g. Including nasal, buccal, rectal, oral, administration; parenterally, e.g. including intravenous, intramuscular, subcutanous administration; or topically; e.g. including epicutaneous, intranasal, intratracheal administration; e.g. in form of coated or uncoated tablets, capsules, injectable solutions or suspensions, e.g. in the form of ampoules, vials, in the form of ointments, creams, gels, pastes, inhaler powder, foams, tinctures, lip sticks, drops, sprays, e.g. or in the form of suppositories. The compounds of the present invention may be administered in the form of a pharmaceutically acceptable salt, or in free form; optionally in the form of a solvate. The compounds of the present invention in the form of a salt exhibit the same order of activity as the compounds of the present invention in free form; optionally in the form of a solvate.

A compound of the present invention may be used for pharmaceutical treatment according to the present invention alone, or in combination with one or more other pharmaceutically active agents. Such other pharmaceutically active agents include e.g. retinoids, e.g. retinoic acid, such as isotretinoin; tretinoin (Roche); adapalene (6-[3-(1-adamantyl)-4-methoxyphenyl]-2-naphthoic acid); oral contraceptives, e.g. 19-nor-17a-pregna-1,3,5(10)-trien-20-in-3,17-diol, 6-Chlor-17-hydroxy-1a,2a-methylen-4,6-pregnadien-3,20-dion, such as Diane® (Schering), antibacterials, such as erythromycins, including erythromycin A, azithromycin, clarithromycin, roxythromycin; tetracyclines, lincosamid-antibiotics, such as clindamycin (methyl 7-chlor-6,7,8-tridesoxy-6-(trans-1-methylpropyl-L-2-pyrrolidin-carboxamido)-1-thio-L-threo-a-D-galacto-octopyranosid), azelaic acid (nonanedionic acid), nadifloxacin; dapsone, benzoyl peroxide; keratolytics, such as salicylic acid; anti-inflammatory agents, such as corticosteroids, pimecrolimus; steroid 5α-reductase inhibitors. For the treatment of breast and endometrial cancer further pharmaceutically active agents include aromatase inhibitors, such as anastrozole, letrozole, exemestane.

Combinations include
  fixed combinations, in which two or more pharmaceutically active agents are in the same pharmaceutical composition,
  kits, in which two or more pharmaceutically active agents in separate compositions are sold in the same package, e.g. with instruction for co-administration; and
  free combinations in which the pharmaceutically active agents are packaged separately, but instruction for simultaneous or sequential administration are given.

In another aspect the present invention provides a pharmaceutical composition comprising a compound of the present invention in association with at least one pharmaceutical excipient, e.g. appropriate carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure, buffers.

In another aspect the present invention provides a pharmaceutical composition according to the present invention, further comprising another pharmaceutically active agent.

Such pharmaceutical compositions may be manufactured according, e.g. analogously to a method as conventional, e.g. by mixing, granulating, coating, dissolving or lyophilizing processes.

In the following example references to temperature are in degree Centigrade and are uncorrected. $^1$HNMR are carried out in $CDCl_3$ if not otherwise indicated.

The following abbreviations are used:
m.p.: melting point
EtAc: ethyl acetate
BOC: tert.butyloxycarbonyl
DMF: N,N-dimethylformamide
RT: room temperature
DMSO: dimethylsulfoxide

EXAMPLE 1

N-[[4-[1-(2-Aminocarbonyl-5-trifluoromethyl-phenyl)]-piperidinyl]-amino]-sulfonyl-3,5-bis-trifluoromethyl-benzamide A) 4-[N-(Aminosulfonyl)benzylamino]-piperidine-1-carboxylic acid tert.butylester A solution of 2.05 g of 4-benzylamino-piperidine-1-carboxylic acid tert.-butyl ester and 3.39 g of sulfamide in 100 ml of 1,2-dimethoxy-ethane is refluxed for ca. 10 hours. From the mixture obtained solvent is evaporated, the evaporation residue obtained is treated with EtAc and unsoluble parts are filtered off. The filtrate obtained is subjected to chromatography on silica gel. 4-[N-(Aminosulfonyl)-benzylamino]-piperidine-1-carboxylic acid tert.butylester is obtained. mp 140-142°. $^1$H-NMR (DMSO) δ: 7.30-7.41 (s/m, 9+2H), 1.64 (m, 2H), 2.53-2.72 (broad, 2H), 3.71 (tt, 1H), 8.83-8.96 (broad, 2H), 4.26 (s, 2H, CH2), 6.86 (bs, 2H, NH), 7.19 (t, 1H), 7.28 (t, 1H), 7.36 (d, 1H). $^{13}$C-NMR (DMSO) δ:28.51, 30.13, 43.35, 47.11, 56.52, 79.12, 127.06, 127.48, 128.49, 140.59, 154.156.

B) N-(1-BOC-4-Piperidinyl-benzylamino)-sulfonyl-3,5-bis-trifluoromethyl-benzamide 280 mg of diisopropyl-ethylamine and 1.28 ml of n-propylphosphonic anhydride (50% solution in DMF) are added to a solution of 400 mg of 4-[N-(aminosulfonyl)-benzylamino]-piperidine-1-carboxylic acid tert.butylester and 560 mg of 3,5-bis-(trifluoromethyl)benzoic acid in 15 ml of DMF. The mixture obtained is stirred for ca. 4 days at RT, solvent is evaporated and the evaporation residue is treated with EtAc and washed with 1 N HCl, sat. $NaHCO_3$ solution and brine and dried. From the dried residue solvent is evaporated and the evaporation residue obtained is subjected to chromatograpy on silica gel. N-(1-BOC-4-Piperidinyl-benzylamino)-sulfonyl-3,5-bis-4-trifluoromethyl-benzamide is obtained.

$^1$H-NMR (DMSO) δ:1.28-1.40 (m, 9+2H), 1.60 (m, 2H), 2.54-2.70 (m, 2H), 3.80-3.94 (m, 2+1H), 4.55 (s, 2H,CH2), 7.18 (t, 1H), 7.27 (d, 1H), 7.37 (d, 1H), 8.26 (s, 1H), 8.46 (s, 2H), 12.6 (broad, 1H, NH).

C) N-(4-Piperidinyl-benzylamino)sulfonyl-3,5-bis-trifluoromethyl-benzamide in the form of a hydrochloride A solution of 650 mg of N-(1-BOC-4-piperidinyl-benzylamino)-sulfonyl-3,5-bis-trifluoromethyl-benzamide in 5 ml of $CH_2Cl_2$ is treated with 60 ml of 3 N HCl (gas) in diethyl-ether. The mixture obtained is stirred for ca. 12 hours and solvent is evaporated. N-(4-Piperidinyl-benzylamino)-sulfonyl-3,5-bis-trifluoromethyl-benzamide in the form of a hydrochloride is obtained. $^1$H-NMR (DMSO) δ:1.72-1.86 (m, 4H), 2.90 (m, 2H), 3.20-3.3 (m, 2H), 4.15 (m, 1H), 4.60 (s, 2H, CH2), 7.31 (t, 1H), 7.40 (t, 1H), 7.48 (d, 1H), 8.38 (s, 1H), 8.48 (s, 2H), 8.48 and 8.75 (broad, 2H, NH).

D) N-[[4-[1-(2-Aminocarbonyl-5-trifluoromethyl-phenyl)]-piperidinyl]-benzylamino]-sulfonyl-3,5-bis-trifluoromethyl-benzamide 430 mg of 2-fluoro-4-trifluoromethyl-benzamide and 430 mg of $K_2CO_3$ are added to a solution of 570 mg of N-(4-piperidinyl-benzylamino)-sulfonyl-3,5-bis-trifluoromethyl-benzamide hydrochloride in 15 ml of DMSO. The mixture obtained is stirred for ca. 4 hours at 150° and $K_2CO_3$ is removed by filtration. Solvent from the filtrate obtained is evaporated and the evaporation residue is subjected to chromatography on silica gel. N-[[4-[1-(2-Aminocarbonyl-5-trifluoromethyl-phenyl)]-piperidinyl]-benzylamino]-sulfonyl-3,5-bis-trifluoromethyl-benzamide is obtained. $^1$H-NMR (DMSO) δ:1.60-1.76 (m, 4H), 2.72 (m, 2H), 3.13 (m, 2H), 3.78 (m, 1H), 4.55 (s, 2H, CH2), 7.14 (t, 1H), 7.23 (t, 1H), 7.26 (d, 1H), 7.32 (d, 1H), 7.41 (d, 1H), 7.59 (broad, 1H, NH), 7.68 (d, 1H), 8.08 (broad, 1H, NH), 8.12 (s, 1H), 8.45 (s, 2H).

E) N-[[4-[1-(2-Aminocarbonyl-5-trifluoromethyl-phenyl)]-piperidinyl]-amino]-sulfonyl-3,5-bis-trifluoromethyl-benzamide 830 mg of N-[[4-[1-(2-aminocarbonyl-5-trifluoromethyl-phenyl)]-piperidinyl]-benzylamino]-sulfonyl-3,5-bis-trifluoromethyl-benzamide are dissolved in 20 ml of MeOH and the mixture obtained is hydrogenated for ca. 12 hours at 40° in the presence of 10% palladium on charcoal. The catalyst is filtered off and the filtrate obtained is subjected to chromatography on silica gel. N-[[4-[1-(2-Aminocarbonyl-5-trifluoromethyl-phenyl)]-piperidinyl]-amino]-sulfonyl-3,5-bis-trifluoromethyl-benzamide is obtained. mp 192-195° C. ¹H-NMR (DMSO) δ:1.58 (m, 2H), 1.94 (m, 2H), 2.77 (m, 2H), 3.11-3.21 (m, 3H), 5.8 (broad, 1H, NH), 7.32 (s, 1H), 7.36 (d, 1H), 7.69 (broad, 1H), 7.74 (d, 1H), 8.16 (s, 1H), 8.22 (broad, 1H), 8.48 (s, 2H).

Analogously to the method as described in example 1 but using appropriate starting materials compounds of formula

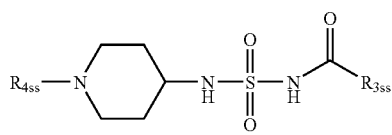

are obtained, wherein $R_{3ss}$ and $R_{4ss}$ are as defined in TABLE 1 having a melting point as defined in TABLE 1:

TABLE 1

| Example | $R_{3ss}$ | $R_{4ss}$ | m.p. |
|---|---|---|---|
| 1 | 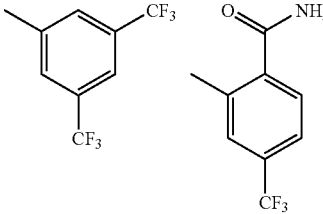 |  | 192-195° |
| 2 | 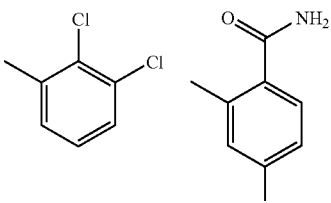 |  | 215-220° |
| 3 | 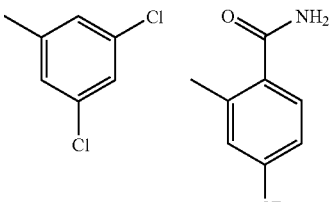 |  | 149-152° |

TABLE 1-continued

| Example | $R_{3ss}$ | $R_{4ss}$ | m.p. |
|---|---|---|---|
| 4 | 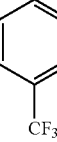 | 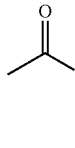 | 190° decomposition |

EXAMPLE 5

3,5-Bis(trifluoromethyl)benzoyl-sulfamic acid N-BOC-piperazineamide

A) N-BOC-piperazine-N'-sulfamate 612 mg of amidosulfonyl chloride in 20 ml of CH₂Cl₂ are added to a solution of 1 g of BOC-piperazine and 1.085 g of triethylamine. The mixture obtained is stirred for ca. 6 hours at 0° and allowed to warm to RT overnight. Solvent of the mixture obtained is evaporated, the evaporation residue obtained is dissolved in ethyl acetate, washed with H₂O, dried and concentrated. The concentration residue obtained is subjected to chromatography on silicagel. N-BOC-piperazine-N'-sulfamate in crystalline form is obtained. m.p.: 167-171°.

B) 3,5-Bis(trifluoromethyl)benzoyl-sulfamic acid N-BOC-piperazineamide

To a solution of 195 mg of N-BOC-piperazine-N'-sulfamate and 148 mg of triethylamine are added 406 mg of 3,5-bis(trifluoromethyl)benzoylchloride in 50 ml of CH₂Cl₂. The mixture obtained is stirred for ca. 20 hours at RT, solvent is evaporated, the evaporation residue obtained is dissolved in EtAc, washed with H₂O, dried and concentrated. The concentration residue obtained is subjected to chromatograpy on silica gel. 3,5-bis(trifluoromethyl)benzoyl-sulfamic acid N-BOC-piperazineamide in crystalline form are obtained. m.p.:185-190°. ¹H-NMR δ:1.4 (s, 9H. BOC), 3.0-3.2 (m, 4H), 3.3-3.5 (m, 4H), 7.78 (s, 1H), 8.28 (s, 2H).

Analogously to the method as described In example 5 but using appropriate starting materials compounds of formula

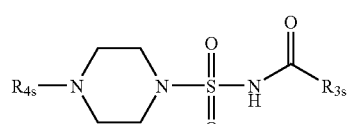

wherein $R_{3s}$ and $R_{4s}$ are defined in TABLE 2, having the melting point as set out in TABLE 2 are obtained:

TABLE 2

| Example | R₃ₛ | R₄ₛ | m.p. |
|---|---|---|---|
| 5 | 3,5-bis(CF₃)phenyl | —C(=O)—O—C(CH₃)₃ | 185-190° |
| 6 | 2,3-dichlorophenyl | —C(=O)—O—C(CH₃)₃ | 172-175° |
| 7 | 3,5-dichlorophenyl | —C(=O)—O—C(CH₃)₃ | 200-203° |
| 8 | 3,5-bis(CF₃)phenyl | —C(=O)—O—CH₂—C₆H₅ | 208-211° |
| 9 | 2,3-dichlorophenyl | —C(=O)—O—CH₂—C₆H₅ | 63-67° |
| 10 | 3,5-dichlorophenyl | —C(=O)—O—CH₂—C₆H₅ | 205-208° |
| 11 | 3,5-bis(CF₃)phenyl | 2-methyl-4-(CF₃)benzamide | 195-197° |
| 12 | 3,5-dichlorophenyl | 2-methyl-4-(CF₃)benzamide | 193-197° |

TABLE 2-continued

| Example | R$_{3s}$ | R$_{4s}$ | m.p. |
|---|---|---|---|
| 13 | 2,3-dichlorophenyl-methyl | 2-methyl-4-(trifluoromethyl)benzamide | 154-157° |
| 14 | 2-(3,5-bis(trifluoromethyl)phenyl)ethyl | tert-butoxycarbonyl | 186-189° |

The invention claimed is:

1. A compound of formula I:

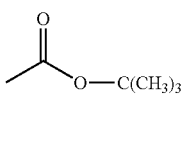

wherein either

R$_1$ and R$_2$ together with the nitrogen atom to which they are attached are piperazinyl, wherein the second nitrogen atom is substituted by (C$_{1-6}$)alkoxycarbonyl or by (C$_{6-18}$)aryl, which (C$_{6-18}$)aryl is substituted by one or more halogen, (C$_{1-6}$)haloalkyl, aminocarbonyl, or R$_1$ is hydrogen and R$_2$ is piperidinyl, attached via a carbon atom of the piperidinyl ring, wherein the nitrogen atom is substituted by (C$_{1-6}$)alkoxycarbonyl or by (C$_{6-18}$)aryl, and R$_3$ is (C$_{6-18}$)aryl or (C$_{6-18}$)aryl(C$_{1-4}$)alkyl, which aryl is substituted by one or more halogen, aminocarbonyl, or (C$_{1-6}$)haloalkyl.

2. A compound of claim 1 selected from the group consisting of compounds of Formula I$_{SS}$:

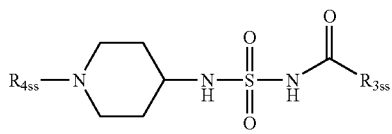

wherein a. R$_{3ss}$ is 3,5-bis(trifluoromethyl)phenyl and R$_{4ss}$ is 2-aminocarbonyl-5-trifluoromethylphenyl,
b. R$_{3ss}$ is 2,3-dichlorophenyl, R$_{4ss}$ is 2-aminocarbonyl-5-trifluoromethylphenyl,
c. R$_{3ss}$ is 3,5-dichlorophenyl R$_{4ss}$ is 2-aminocarbonyl-5-trifluoromethylphenyl, and
d. R$_{3ss}$ is 3,5-bis(trifluoromethyl)phenyl and R$_{4ss}$ is tert.butoxycarbonyl.

3. A compound of claim 1 which is a compound of formula

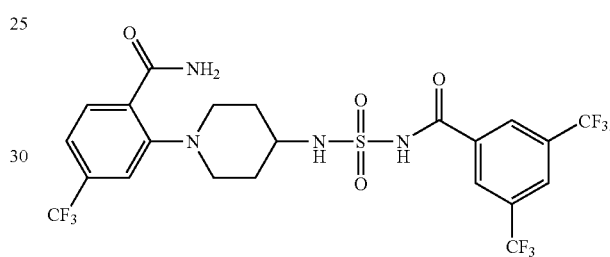

4. A compound of claim 1 selected from the group consisting of compounds of Formula I$_S$:

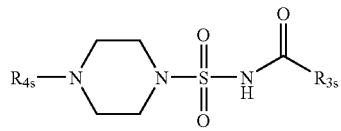

wherein a. R$_{3s}$ is 3,5-bis(trifluoromethyl)phenyl and R$_{4s}$ is tert.butoxycarbonyl,
b. R$_{3s}$ is 2,3-dichlorophenyl and R$_{4s}$ is tert.butoxycarbonyl,
c. R$_{3s}$ is 3,5-dichlorophenyl and R$_{4s}$ is tert.butoxycarbonyl,
d. R$_{3s}$ is 3,5-bis(trifluoromethyl)phenyl and R$_{4s}$ is benzyloxycarbonyl,
e. R$_{3s}$ is 2,3-dichlorophenyl and R$_{4s}$ is benzyloxycarbonyl,
f. R$_{3s}$ is 3,5-dichlorophenyl and R$_{4s}$ is benzyloxycarbonyl,
g. R$_{3s}$ is 3,5-dichlorophenyl and R$_{4s}$ is benzyloxycarbonyl,
h. R$_{3s}$ is 3,5-bis(trifluoromethyl)phenyl and R$_{4s}$ is 2-aminocarbonyl-5-trifluoromethylphenyl,
i. R$_{3s}$ is 3,5-dichlorophenyl and R$_{4s}$ is is 2-aminocarbonyl-5-trifluoromethylphenyl,
j. R$_{3s}$ is 2,3-dichlorophenyl and R$_{4s}$ is is 2-aminocarbonyl-5-trifluoromethylphenyl, and
k. R$_{3s}$ is 2-(3,5-bis(trifluoromethyl)phenyl)ethyl and R$_{4s}$ is is tert.butoxycarbonyl.

5. A compound of claim 1 in the form of a salt.

6. A method of treatment of disorders mediated by the action of steroid sulfatase which treatment comprises administering to a subject in need of such treatment an effective amount of a compound of claim 1, wherein the disorder is selected from the group consisting of acne, seborrhea, androgenic alopecia. hirsutism, breast cancer, and.

7. A pharmaceutical composition comprising a compound of claim 1 in association with at least one pharmaceutical excipient.

8. A pharmaceutical composition according to claim 7, further comprising another pharmaceutically active agent.

\* \* \* \* \*